United States Patent [19]

Di Toro et al.

[11] Patent Number: 4,459,239

[45] Date of Patent: Jul. 10, 1984

[54] CHLOROFORMATES OF ALKYL ESTERS OF C-ALKYL- OR C-HALOALKYL TARTRONIC ACIDS AND PROCESS FOR THEIR PREPARATION

[75] Inventors: Vincenzo Di Toro, Como; Franco Gozzo; Pier M. Boschi, both of San Donato Milanese, all of Italy

[73] Assignee: Montedison S.p.A., Milan, Italy

[21] Appl. No.: 338,619

[22] Filed: Jan. 11, 1982

[30] Foreign Application Priority Data

Jan. 12, 1981 [IT] Italy .................................. 19089 A/81

[51] Int. Cl.$^3$ .............................................. C07C 69/96
[52] U.S. Cl. ...................................... 260/463; 548/227
[58] Field of Search ........................................... 260/463

[56] References Cited

U.S. PATENT DOCUMENTS 3,823,175  7/1974  Exner et al. ......................... 260/463
4,342,773  8/1982  Di Toro et al. ..................... 548/226

Primary Examiner—Donald G. Daus
Assistant Examiner—M. C. Eakin

[57] ABSTRACT

Chloroformates of alkyl esters of C-alkyl or C-haloalkyl tartronic acids of the general formula:

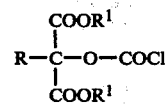

in which:
R represents an alkyl or haloalkyl group having from 1 to 5 carbon atoms, and
$R^1$ represents an alkyl group having from 1 to 5 carbon atoms, may be prepared by reaction of phosgene in an inert solvent with the corresponding ester of the C-alkyl-tartronic acid of the desired compound at a temperature of from 0° to 20° C. in the presence of at least a stoichiometric amount of a tertiary amine.

3 Claims, No Drawings

CHLOROFORMATES OF ALKYL ESTERS OF C-ALKYL- OR C-HALOALKYL TARTRONIC ACIDS AND PROCESS FOR THEIR PREPARATION

Chloroformates of alkyl esters of C-alkyl or C-haloalkyl tartaric acids are not known.

THE PRESENT INVENTION

This invention relates to chloroformates of alkyl esters of C-alkyl or C-haloalkyl-tartronic acids and to their preparation. These compounds are particularly useful in the synthesis of oxazolidindione derivatives, which have utility as pesticides and analgesics.

German Offenlegungsschrift No. 2,906,574 discloses the synthesis of N-phenyl-1,3-oxazolidin-2,4-dione fungicides of the general formula (III) according to the following reaction scheme:

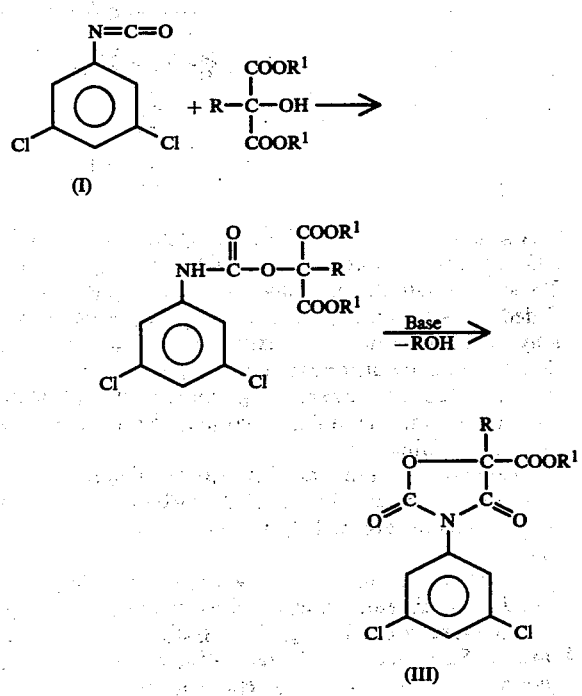

It has been found that by employing the corresponding chloroformate of compound (II) it is possible to use 3,5-dichloroaniline as a starting material instead of the isocyanate (I):

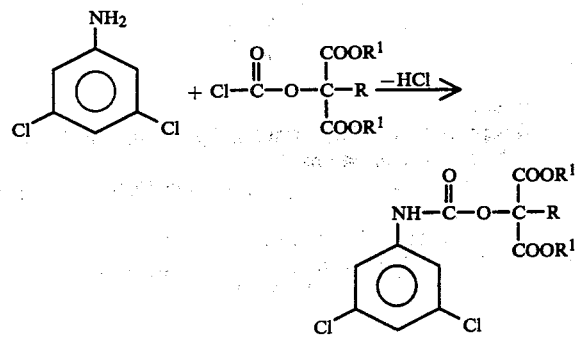

This reaction occurs with optimum yields, and makes it possible to reduce the consumption of the expensive 3,5-dichloroaniline by avoiding the necessity of converting it to the isocyanate.

It is an object of the present invention to provide chloroformates of alkyl esters of C-alkyl or C-haloalkyl-tartronic acids.

Alkyl esters of C-alkyl or C-haloalkyl-tartronic acids can be prepared by the process disclosed in applicant's copending companion application, Ser. No. 338,620 also filed on Jan. 11, 1982.

According to the present invention there are provided chloroformates of alkyl esters of C-alkyl- or C-haloalkyl-tartronic acid of the general formula:

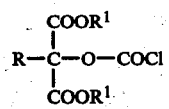

in which:

R represents an alkyl or a haloalkyl group having from 1 to 5 carbon atoms, and $R^1$ represents an alkyl group having from 1 to 5 carbon atoms.

The compounds of the invention may be prepared by dissolving, at room temperature, phosgene in an inert solvent, e.g. benzene, toluene, or aliphatic hydrocarbons, and thereafter adding thereto a substantially stoichiometric amount (or an amount slightly lower than the stoichiometric amount) of the alkyl ester of the selected C-alkyl- or C-haloalkyl-tartronic acid, at a temperature in the range of from 0° to 20° C.

At least a stoichiometric amount, in respect of the ester, of a tertiary amine, preferably pyridine, is then added to the reaction mixture at a temperature below 20° C. On completion of the reaction any excess phosgene may be removed by bubbling an inert gas into the mixture or by distillation. An amount of water sufficient to form two distinctly separate phases is then added at a temperature not exceeding 30° C.

Finally, the two phases are separated, the organic phase is washed and dried and the desired chloroformate is isolated by conventional techniques.

The resulting chloroformates are oils which can be distilled at reduced pressure.

The invention will now be illustrated by the following Examples.

EXAMPLE 1

Preparation of 1,1-diethoxycarbonyl-ethyl-chloroformate

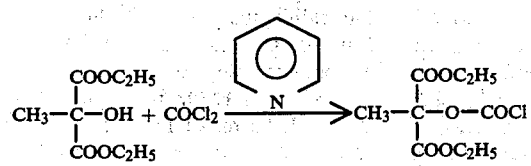

| | molecular weight: | 190.193 (1) | 98.924 (2) | 79.098 (3) | 252.652 |
|---|---|---|---|---|---|

| Compound | Quantity | | |
|---|---|---|---|
| 1 | 387.06 g | = 2.035 | moles |
| 2 | 240 g | = 2.4 | moles |
| 3 | 274 g | = 2.2 | moles |

A solution of $COCl_2$ in 2 l of benzene or toluene was prepared by bubbling gas therethrough at room temperature.

The solution was cooled to 0° C. with ice and salt, whereupon Compound No. 1 was added over a period of 5 minutes during which the temperature rose from 0° to 5° C.

Maintaining the temperature below 10° C., pyridine was added dropwise, whereupon the mixture was stirred for three hours at room temperature. The excess $COCl_2$ was removed by bubbling air and then destroyed by addition of 100 ml of $H_2O$, ensuring that the temperature did not rise above 25° C.

The aqueous phase was separated and the organic solution was washed with 4% HCl, dried over $Na_2SO_4$ and concentrated at reduced pressure.

Water pump-distillation yielded 465 grams of a colorless oil having a boiling point of 130° to 131° C./15 mm Hg and a purity of 98% (liquid gas chromatography). The yield was 90%.

Characterization: I.R. (film): $\nu(CO)=1740-1790$ cm$^{-1}$.

N.M.R. (CD Cl$_3$/TMS): $\delta 1.3$ (trip., $CH_2$—$CH_3$), $\delta 1.9$ (sing. $CH_3$), $\delta 4.3$ (quadr., $CH_2$—$CH_3$).

EXAMPLE 2

Preparation of
1,1-dimethoxycarbonyl-propyl-chloroformate

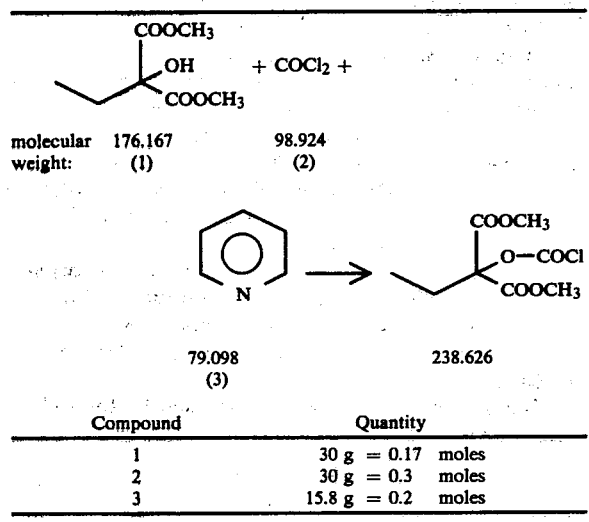

| Compound | Quantity |
|---|---|
| 1 | 30 g = 0.17 moles |
| 2 | 30 g = 0.3 moles |
| 3 | 15.8 g = 0.2 moles |

Phosgene was dissolved in 200 ml of benzene, the solution was cooled to 0° C., compound No. (1) was then added and pyridine was dropped thereinto at a temperature below 10° C. The reaction mixture was stirred 3 hours at room temperature.

After addition of 50 ml of $H_2O$, the organic solution was washed twice with 50 ml of HCl at 3.7%. After evaporation of the solvent, the residue was distilled with a water pump.

31 g of a colourless oil were obtained having a boiling point of 123° to 124° C./15 mm Hg and a purity of 98% (gas chromatography). The yield was 90%.

Characterization: I.R. (film): $\nu(CO)=1740-1800$ cm$^{-1}$.

N.M.R. (CD Cl$_3$/TMS): $\delta 1.0$ (tripl., $CH_2$—$CH_3$), $\delta 2.2$ (quadr., $CH_2$—$CH_3$), $\delta 3.9$ (sing., $CH_3$).

EXAMPLE 3

The following example is given to show how a well known fungicide, 5 (3,5-dichlorophenyl)-5-methyl-5-carboethoxy-1,3-oxazolidine-2,4-dione (D.O.S. No. 2,906,574) is prepared with high yield from 1,1-diethoxycarbonyl-ethyl-chloroformate.

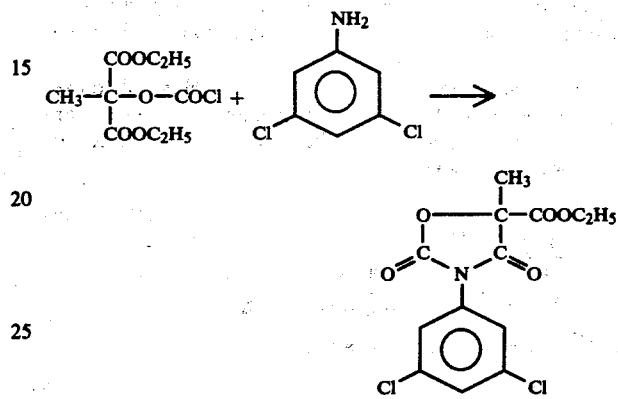

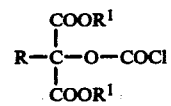

A solution of 32.4 g of (3,5-dichlorophenyl) aniline in 200 cc of toluene was heated to the boiling temperature. To such solution, maintained at reflux, there were added, in 40 minutes, 52 g of 1,1-diethoxycarbonyl-ethyl-chloroformate. The mixture was heated for additional 40 minutes at reflux; thereafter, 168 cc of toluene were distilled. To the remaining solution 4 g of pyridine were added and the mixture was heated for 2 hours 15 minutes at reflux.

Thereafter, the ethyl alcohol was distilled off.

The solution was then cooled to 80° C., 180 cc of ethyl alcohol were added; a white solid was precipitated.

The mixture was cooled down to 20° C., the white solid was filtrated, washed with ethanol and dried. There were obtained 59 g of 5-(3,5-dichlorophenyl)-5-methyl-5-carboethoxy-1,3-oxazolidine-2,4-dione, having M.P. 111°-112° C. The yield was about 88%.

We claim:

1. Chloroformates of alkyl esters of C-alkyl- or C-haloalkyl-tartronic acid of the general formula:

$$\begin{array}{c} COOR^1 \\ | \\ R-C-O-COCl \\ | \\ COOR^1 \end{array}$$

in which:

R represents an alkyl or haloalkyl group having from 1 to 5 carbon atoms, and $R^1$ represents an alkyl group having from 1 to 5 carbon atoms.

2. 1,1-diethoxycarbonyl-ethyl-chloroformate.
3. 1,1-dimethoxycarbonyl-propyl-chloroformate.

* * * * *